United States Patent
Churchill et al.

(10) Patent No.: US 7,952,721 B2
(45) Date of Patent: May 31, 2011

(54) OPTICAL LINEAR AND ROTATION DISPLACEMENT SENSOR

(75) Inventors: David L. Churchill, Burlington, VT (US); Steven W. Arms, Williston, VT (US)

(73) Assignee: Microstrain, Inc., Williston, VT (US)

(*) Notice: Subject to any disclaimer, the term of this patent is extended or adjusted under 35 U.S.C. 154(b) by 297 days.

(21) Appl. No.: 12/202,241

(22) Filed: Aug. 30, 2008

(65) Prior Publication Data

US 2009/0059206 A1    Mar. 5, 2009

Related U.S. Application Data

(60) Provisional application No. 60/968,992, filed on Aug. 30, 2007.

(51) Int. Cl.
*G01B 11/02*    (2006.01)
(52) U.S. Cl. ....................................................... 356/496
(58) Field of Classification Search .................. 356/496, 356/498
See application file for complete search history.

(56) References Cited

U.S. PATENT DOCUMENTS

| | | | |
|---|---|---|---|
| 5,596,595 A | 1/1997 | Tan | |
| 5,686,720 A | 11/1997 | Tullis | |
| 5,786,804 A | 7/1998 | Gordon | |
| 5,818,861 A | 10/1998 | Tan | |
| 6,151,015 A | 11/2000 | Badyal | |
| 6,195,475 B1 | 2/2001 | Beausoleil, Jr. | |
| 6,281,882 B1 | 8/2001 | Gordon | |
| 6,289,030 B1 | 9/2001 | Charles | |
| 6,433,780 B1 | 8/2002 | Gordon | |
| 6,489,945 B1 | 12/2002 | Gordon | |
| 6,600,310 B2 | 7/2003 | Nyce | |
| 6,621,483 B2 | 9/2003 | Wallace | |
| 6,704,183 B2 | 3/2004 | Stafford | |
| 7,081,693 B2 | 7/2006 | Hamel | |
| 7,256,505 B2 | 8/2007 | Arms | |
| 2002/0130835 A1 | 9/2002 | Brosnan | |
| 2002/0158300 A1 | 10/2002 | Gee | |
| 2002/0190953 A1 | 12/2002 | Gordon | |
| 2003/0034959 A1 | 2/2003 | Davis | |
| 2004/0084610 A1 | 5/2004 | Leong | |
| 2004/0129095 A1 | 7/2004 | Churchill | |
| 2004/0189593 A1 | 9/2004 | Koay | |
| 2005/0024336 A1 | 2/2005 | Xie | |
| 2005/0024623 A1 | 2/2005 | Xie | |
| 2005/0083303 A1 | 4/2005 | Schroeder | |
| 2007/0247636 A1* | 10/2007 | Matsuoka | 356/498 |

FOREIGN PATENT DOCUMENTS

| | | |
|---|---|---|
| JP | 5196432 A | 8/1993 |
| JP | 08122340 A | 5/1996 |
| JP | 2007178137 A | 7/2007 |

OTHER PUBLICATIONS

No author, "ADNB-6011-EV and ADNB-6012-EV High Performance Laser Mouse Bundles," data sheet, Jan. 19, 2007, pp. 1-52, Avago Technologies, San Jose, CA.

* cited by examiner

*Primary Examiner* — Patrick J Connolly
(74) *Attorney, Agent, or Firm* — James Marc Leas

(57) ABSTRACT

A system includes a measuring tool, a fixture, and a rotatable target. The measuring tool includes a light source, an imaging device, and an electronic circuit. The fixture allows the rotatable target to rotate about an axis. The rotatable target includes a surface having microscopic asperities. The imaging device is mounted to provide a sequence of images derived from said microscopic asperities. The electronic circuit is connected to the imaging device for measuring rotation of the rotatable target from the sequence of images.

54 Claims, 17 Drawing Sheets

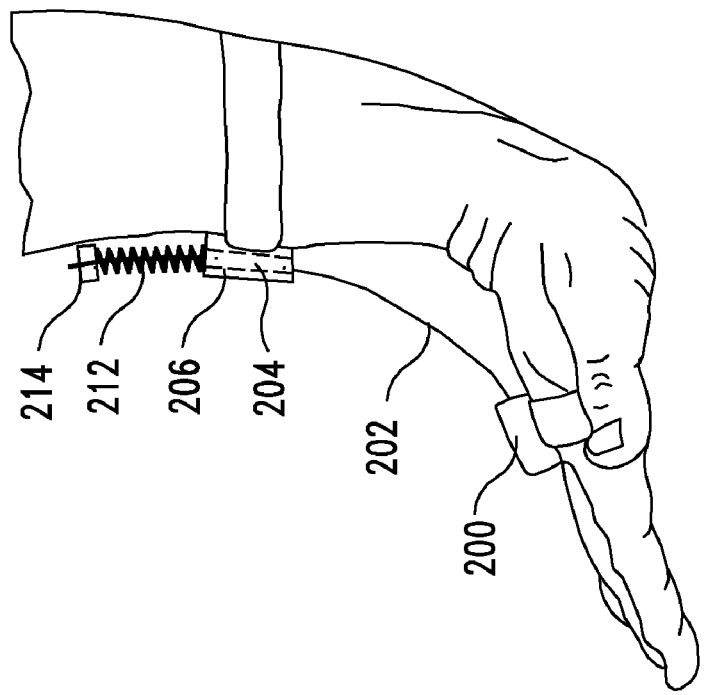
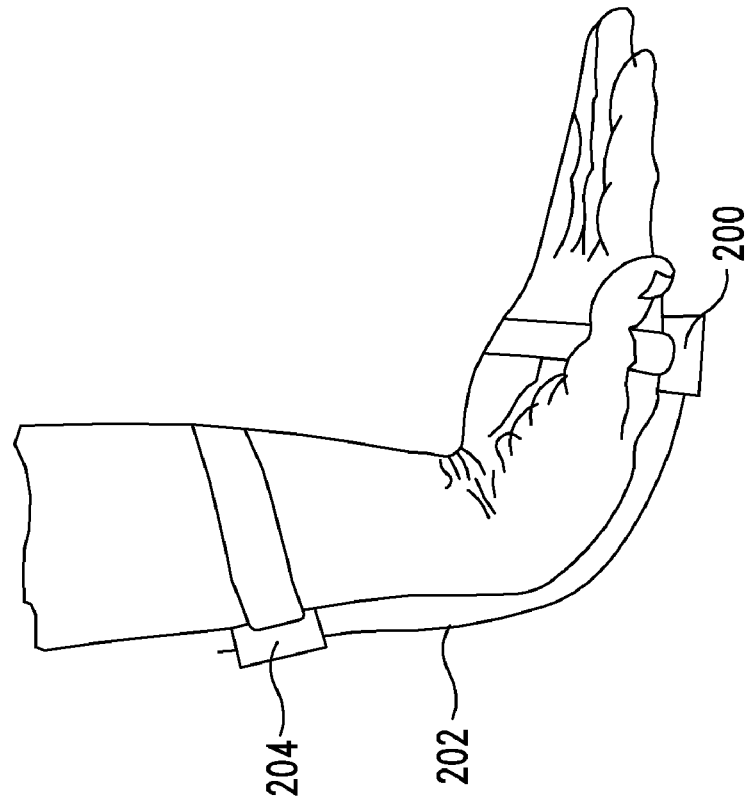
FIG. 9b
FIG. 9a

OPTICAL LINEAR AND ROTATION DISPLACEMENT SENSOR

RELATED PATENT APPLICATIONS AND PRIORITY

This application claims priority of Provisional Patent Application 60/968,992, filed Aug. 30, 2007, incorporated herein by reference.

FIELD

This patent application generally relates to optical displacement sensors. More particularly it relates to non-contact optical displacement sensors.

BACKGROUND

Many electrical and mechanical applications involve measuring relative motion between two objects. This motion may include translation, rotation, or a combination of both. A wide variety of sensing technologies have been developed to accomplish this task.

An important category of such displacement sensors are those that accomplish their measurement in a non-contacting manner. In this category no direct mechanical connection exists between the two objects or between the measuring device, which may be mounted to move with one of the objects, and the other object. The advantages of non-contacting measurement include: zero friction, high immunity to contamination, zero wear, long lifetime, inherent electrical safety, and physical isolation of the two moving objects from one-another. In many cases, mechanical guides or bearings are used to constrain the relative motion of one or both of the objects to desired directions, and these can generally be implemented without compromising the main advantages of the non-contacting sensors themselves.

Non-contacting displacement sensors include optical sensors and magnetic sensors. In magnetic sensors, magnetic field domains are established on one of the objects, either with permanent magnets, or with energized coils. A magnetic flux detector mounted to the opposing object detects the relative motion by sensing the change in magnetic flux.

In optical sensors, one object, called the "target" object, includes regularly spaced marks. Often, multiple tracks of marks are used to provide the ability to distinguish the direction of movement, and some absolute starting point. Mounted to the second object, called the "reference" object, is a light source and an optical detector which can image the marks on the target. By tracking the movement of the marks in the image field, the system can detect and measure relative motion between the target and the reference objects. Such sensors have been configured to measure either translation, with the marks configured along a straight line, or rotation, with the marks configured around the circumference of a circle on a plane, such as a disk or with marks configured around the surface of a cylinder, such as a drum.

With either the magnetic or the optical non-contacting sensors the target object was often engineered with the application of magnetic domains or visible marks. One large field of use for optical displacement sensors that did not require an engineered surface has been optical computer mouse sensors that inherently measure the relative displacement between the reference object, the mouse, and the target object, a surface such as a table top. Optical computer mouse sensors have been specifically designed to allow for the use of non-engineered targets with no marks added to the target surface. Instead the optical mouse sensors use whatever naturally existing visible features are present as the target "marks" to be imaged. Those computer mouse sensors that illuminate the target with coherent laser light have been particularly well adapted to using a wide variety of surface materials as the target. The coherent light reflecting from microscopic asperities present in nearly all surface materials generates a high contrast interference speckle pattern that is ideal for imaging and mouse position detection. Microscopic asperities are unintentionally occurring unevenness or roughness of a surface. They may have a size in the range from the wavelength of light used to hundreds of microns. They may typically have a dimension of a fraction of a micron to tens of microns. They may be randomly distributed along the surface. Each is usually different from others.

Applicants recognized further applications of such non-contacting optical sensors, and these applications are provided by the following description.

SUMMARY

One aspect of the present patent application is a system that includes a measuring tool, a fixture, and a rotatable target. The measuring tool includes a light source, an imaging device, and an electronic circuit. The fixture allows the rotatable target to rotate about an axis. The rotatable target includes a surface having microscopic asperities. The imaging device is mounted to provide a sequence of images derived from said microscopic asperities. The electronic circuit is connected to the imaging device for measuring rotation of the rotatable target from the sequence of images.

Another aspect is a system that includes a measuring tool, a first fixture, a moveable target, and a first axis. The measuring tool includes a light source, an imaging device, and an electronic circuit. The first fixture constrains the moveable target to at least one from the group consisting of translation along the first axis and rotation about the first axis. The moveable target includes a surface having microscopic asperities. The imaging device is mounted to provide a sequence of images derived from the microscopic asperities. The electronic circuit is connected to the imaging device for measuring movement of the moveable target from the sequence of images.

Another aspect is a system that includes an elongate member and a measuring tool. The measuring tool includes a light source, an imaging device, and an electronic circuit. The elongate member has a surface and the imaging device is mounted to image the surface. The measuring tool measures at least one from the group consisting of translation and rotation of the elongate member from the images of the surface.

BRIEF DESCRIPTION OF THE DRAWINGS

The foregoing will be apparent from the following detailed description, as illustrated in the accompanying drawings, in which:

FIGS. 9a and 9b are side views of a hand, wrist, and arm of a person with a measuring tool of the present patent application mounted thereon for measuring rotational displacement of the wrist;

DETAILED DESCRIPTION

The present applicants recognized advantage if a non-planar target object did not need to be engineered in any way. This would allow for the ability to measure displacement and rotation of target objects that are not designed specifically for displacement sensing. For example, the present applicants considered the case where the depth of insertion of a disposable acupuncture needle into a patient is to be measured. As described herein below they found a way to implement a non-contacting sensor that uses the surface of a standard acupuncture needle as its target.

The present applicants recognized that computer mouse sensors can be used to accurately detect the translation and rotation of non-planar targets, such as elongate members, including wires, threads, filaments, needles, tubes, catheters, rods and tapes. They found that no special preparation of the surface of the wire or needle was required. They found that this optical sensing technology was ideal for measuring the insertion depth, and rotation of acupuncture needles, catheters, hypodermic needles, biopsy needles, and other similar devices into the human body. Since these objects are typically disposable, and low cost, it has not generally been practical to include engineered markings into their surface for the purpose of displacement measurement. The description below provides ability to use the naturally occurring microscopic asperities in their surfaces as the imaging target to measure both axial displacement and rotation of the needle about is axis.

Figure 1:
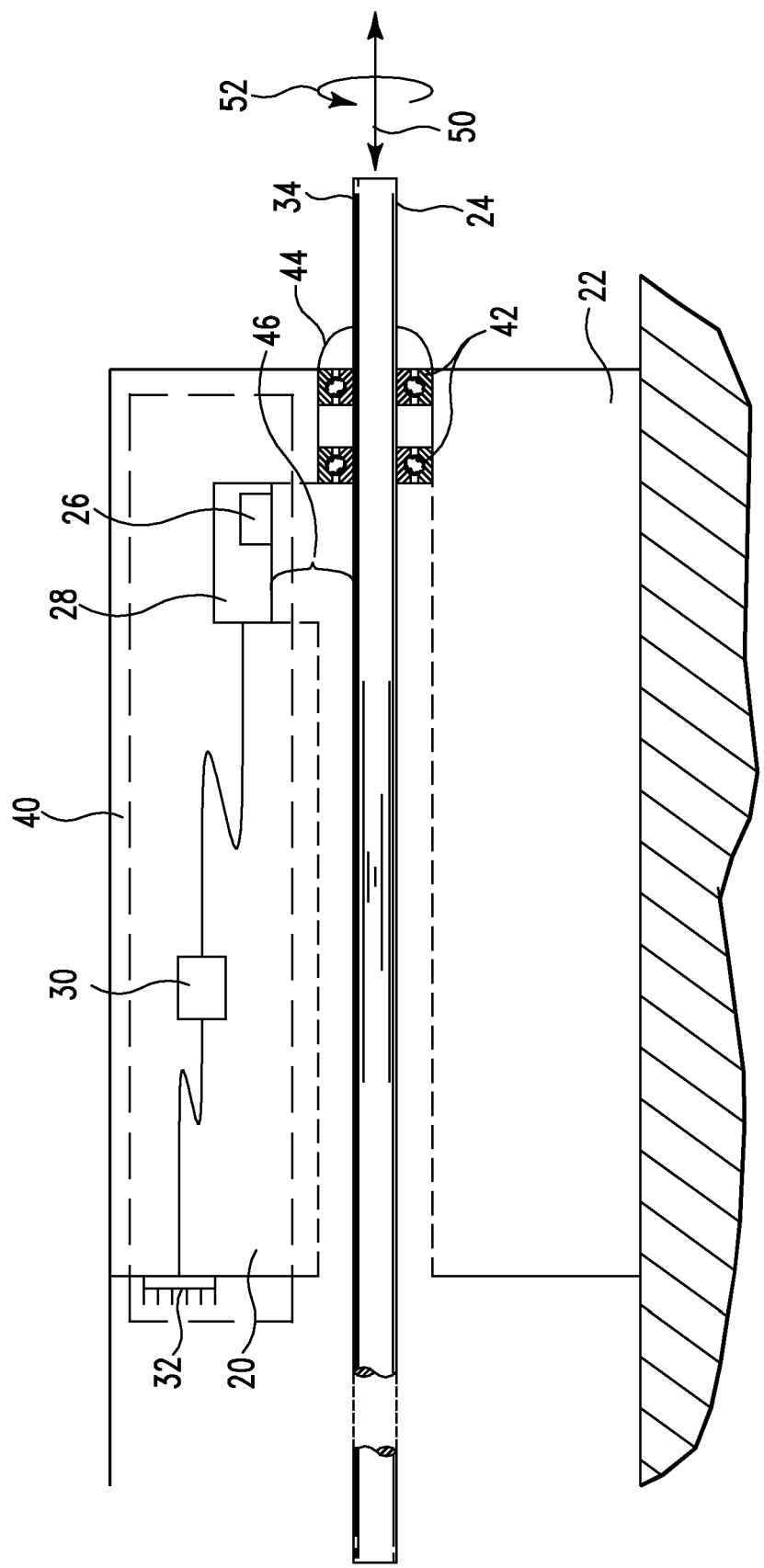
FIG. 1 is a cross sectional view of a measuring tool of the present patent application mounted for measuring linear and/or rotational displacement of a moveable target.

A system includes measuring tool 20, fixture 22, and moveable target 24, as shown in FIG. 1. Measuring tool 20 includes light source 26, imaging device 28, electronic circuit 30, and connector 32. Fixture 22 constrains movement of moveable target 24 to translation along an axis and/or rotation about the axis. Moveable target 24 includes surface 34 having imageable features 36, that may be manufactured into moveable target 24 or that may be inherent in the surface of moveable target 24. Imaging device 28 is mounted to provide a sequence of images of imageable features 36. Electronic circuit 30 is connected to imaging device 28 for determining displacement of imageable features 36 from the sequence of images.

Light source 26 and imaging device 28 may be included in a single device, such as the ADNS-6006 and the ADNS-6010 optical navigation sensor available commercially from Avago Technologies, Andover, Mass. These ADNS devices are commonly used in computer mouse applications. Imaging device 28 of the ADNS devices contains an image acquisition system, a digital signal processor (DSP), and a four wire serial port. It measures changes in position by optically acquiring sequential images of the target surface. The DSP mathematically correlates visible features of the target in sequential images, and computes the delta x and delta y relative displacement values for each time increment. The time increment can be the same between sequential images.

Moveable target 24 may be an elongate member, such as wire, fishing line, chord, rod, tube, pipe, electrical wire, optical cable, or tape. Moveable target 24 can be a needle, such as an acupuncture needle or a hypodermic needle, or a portion of such a needle. Moveable target 24 can be superelestic to avoid breakage. Displacement of moveable target 24 is measured by displacement of imageable features 36 on surface 34. Imageable features 36 may be manufactured targets, surface imperfections, or the laser speckle pattern caused by interference of light reflected off of microscopic asperities, irregularities in the surface, that are used by the ADNS devices, as described in U.S. Pat. No. 5,596,595, "Current and heat spreading transparent layers for surface-emitting lasers," U.S. Pat. No. 5,686,720 "Method and device for achieving high contrast surface illumination," U.S. Pat. No. 5,786,804 "Method and system for tracking attitude," U.S. Pat. No. 5,818,861 "Vertical cavity surface emitting laser with low band gap highly doped contact layer," U.S. Pat. No. 6,151,015 "Pen like computer pointing device," U.S. Pat. No. 6,195,475 "Navigation system for handheld scanner," U.S. Pat. No. 6,281,882 "Proximity detector for a seeing eye mouse," U.S. Pat. No. 6,289,030 "Fabrication of semiconductor devices," U.S. Pat. No. 6,433,780 "Seeing eye mouse for a computer system," U.S. Pat. No. 6,489,945 "Method and system for tracking attitude," U.S. Pat. No. 6,621,483 "Optical screen pointing device with inertial properties," U.S. Pat. No. 6,704,183 "Fault detection in a LED bias circuit," U.S. patent application with Ser. No.

10/217,725, "Seeing Eye Mouse For A Computer System," and published US patent applications 20020130835 "Portable electronic device with mouse-like capabilities," 20020158300 "Fault tolerant electrical circuit and method," 20020190953 "Seeing eye mouse for a computer system," 20030034959 "One chip USB optical mouse sensor solution," 20040084610 "Optical navigation sensor with integrated lens," 20040189593 "Optical mouse adapted for use on glass surfaces," 20050024336 "Method and device for optical navigation," 20050024623 "Method and device for optical navigation," 20050083303 "Tracking motion using an interference pattern," all of which are incorporated herein by reference.

Fixture 22 supports and guides moveable target 24 and may include housing 40, bearings 42, and flexible boot 44. Housing 40 and flexible boot 44 provide environmental protection for moveable target 24 while it is being imaged with imaging device 28. Bearings 42 may be bushings or jewel bearings, as described in commonly assigned U.S. patent application Ser. No. 10/677,578, filed Oct. 2, 2003 , or they may be ball bearings, that permit moveable target 24 to slide or roll with low friction and which guide moveable target 24 so it remains in position for imaging with imaging device 28. Housing 40 includes opening 46 that allows light from light source 26 to exit and light reflected from surface 34 of moveable target 24 to be recorded by imaging device 28.

Electronic circuit 30, includes a processor, and may include other electronic components, as described in the above listed patents. Electronic circuit 30 receives data from the imaging device 28, accumulates the changes, and stores them in memory. Electronic circuit 30 can also include calibration data to convert the raw data into linear and/or rotational travel. Electronic circuit 30 can also be used to adjust parameters, including resolution and data rate, and to keep track of time. In one embodiment absolute measurement is included by providing a manufactured index reference on moveable target 24 from which rotational and translational position is referenced. Electronic circuit 30 can then be used to accumulate the rotational and translational displacement from that reference.

In use, light source 26 shines light through opening 46 in housing 40 onto surface 34 of moveable target 24 while moveable target 24 is pulled, pushed, or rotated through fixture 22. Light source 26 may be a laser, as provided in the ADNS-6006 and the ADNS-6010 optical navigation sensors and as described in the above listed patents. The speckle light pattern reflected from surface 34 is captured by imaging device 28. Sequential images of the speckle pattern or of imageable features 36 on surface 34 of moveable target 26 are captured and analyzed in the included DSP. Electronic circuit 30 determines displacement of moveable target 24 from the accumulation of displacements of these recognized imageable features 36 in the sequential images.

Measuring tool 20 is positioned so that light source 26 is a specified distance D from surface 110 of moveable target 82. Distance D is typically in the range from about 2.1 to about 2.7 mm.

Connector 32 may include pins for power and ground, as well as pins for digital output for linear and rotary motion, and pins for analog output for digital and rotary motion. Connector 32 may be connected to a measurement system that may display, record and communicate the data, for example, to an oscilloscope, personal computer, or processor, or to a server of the internet. Connector 32 may be connected to a measurement and control system that uses the data to provide feedback to control movement of target 24 by providing control over an actuator connected to target 24 or by providing a warning. In another embodiment, wireless communication can be used, such as bluetooth, wifi, or an IEEE 802.15.4 standard. Power can be provided with a battery. Power can also be provided with a wired connection from a power supply connected to a wall outlet. Power can also be provided using energy harvesting, as described in commonly assigned U.S. Pat. No. 7,081,693, and US patent application US 2005-0017602, incorporated herein by reference.

Measuring tool 20 can be used as described in commonly assigned U.S. patent application, Ser. No. 12/173,017, incorporated herein by reference, for monitoring and reporting human motion. It can also be used to monitor displacements of parts in vehicles, such as ailerons and flaps on airplanes, motion of machine tools, and motion of an acupuncture needle. For example, measuring tool 20 can measure and/or control linear motion and/or rotational motion of a hydraulic or pneumatic cylinder on machinery such as earth moving equipment or on a vehicle, such as an airplane or helicopter. It may also be used to measure, track, and/or control linear and/or rotational motion of a biopsy needle, a hypodermic needle, a catheter, or an acupuncture needle. For example, depth of insertion of the acupuncture needle and the amount of needle rotation can be measured without the need to provide marks on the needle. It can also be used to measure hand movements that directs movement of animated characters on a display of a video game or that directs movement of a cursor on a computer display.

Moveable target 24 can be any length from fractions of an inch to miles long. While the above listed Hewlett Packard and Agilent patents describe a mouse that keeps track of displacements along x and y directions in a plane, the present applicants found that the device can be used to measure displacement along axis 50 of moveable target 24 and around axis 50 from rotation 52 of moveable target 26. If moveable target 24 is an elongate member, such as a wire, it can have a length to width ratio of more than ten to one. It can also have a length to width ratio of more than one hundred to one.

The present inventors calibrated an ADNS-6006 optical navigation sensor from Avago Technologies, commonly used in computer mouse applications, to accurately convert its sensor raw output into measurements of linear and rotational displacement of a wire in units of millimeters and radians.

From linear and rotational displacement information, linear velocity and acceleration and rotational velocity and acceleration of the target can be calculated by electronic circuit 30 used to accumulate the data and keep track of time. A precision time keeper can be included, such as part number Maxim DS 3231 and position and rotational data accumulated in memory can be time stamped. A non-volatile memory can be included to store this data.

Figure 2:
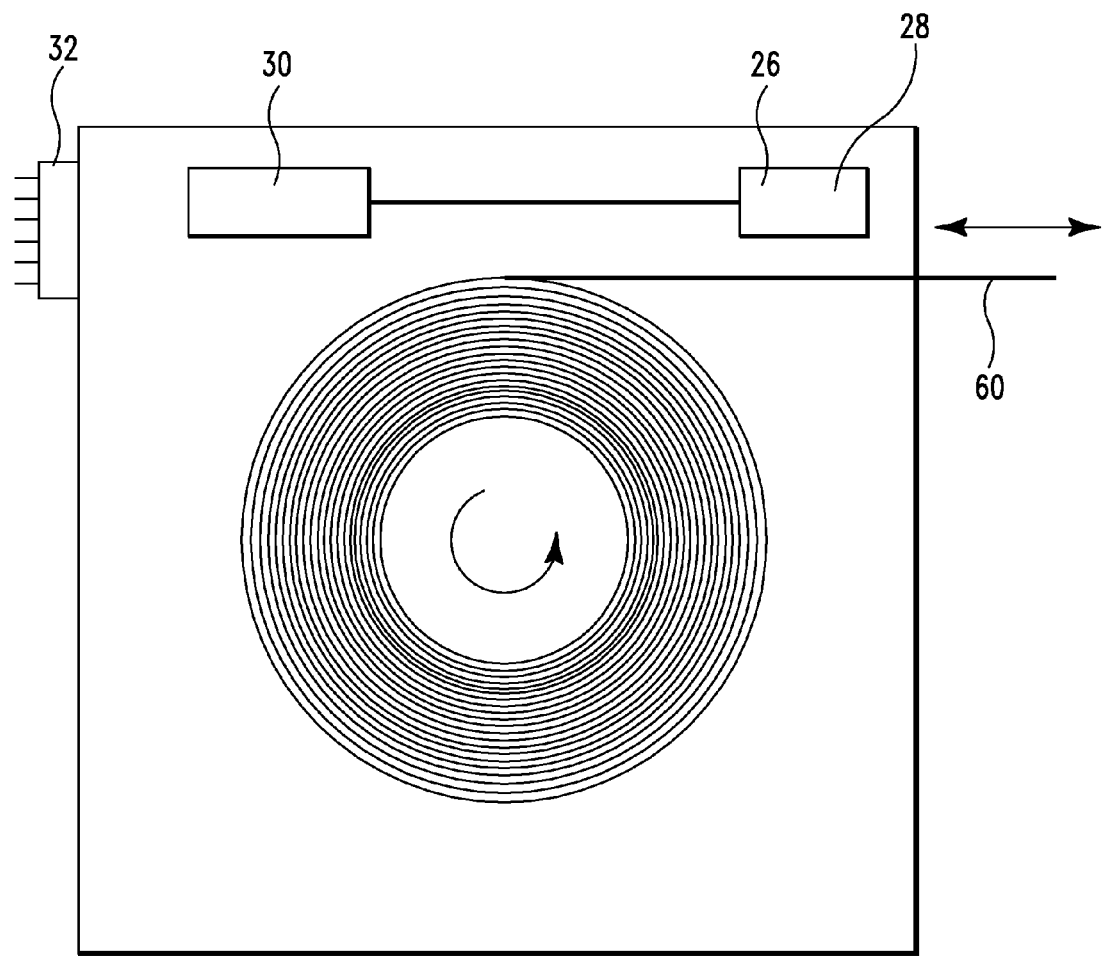
FIG. 2 is a cross sectional view of a measuring tool of the present patent application mounted for measuring linear displacement of a draw wire extending from a spring loaded spool.

In one embodiment wire 60 is drawn from wire wound around spring loaded spool 62 while imaging device 28 takes images of laser light originating in light source 26 and reflected from wire 60 to determine length of wire drawn in electronic circuit 30 while data is obtained from 6 pin connector 32, as shown in FIG. 2.

Figure 3:
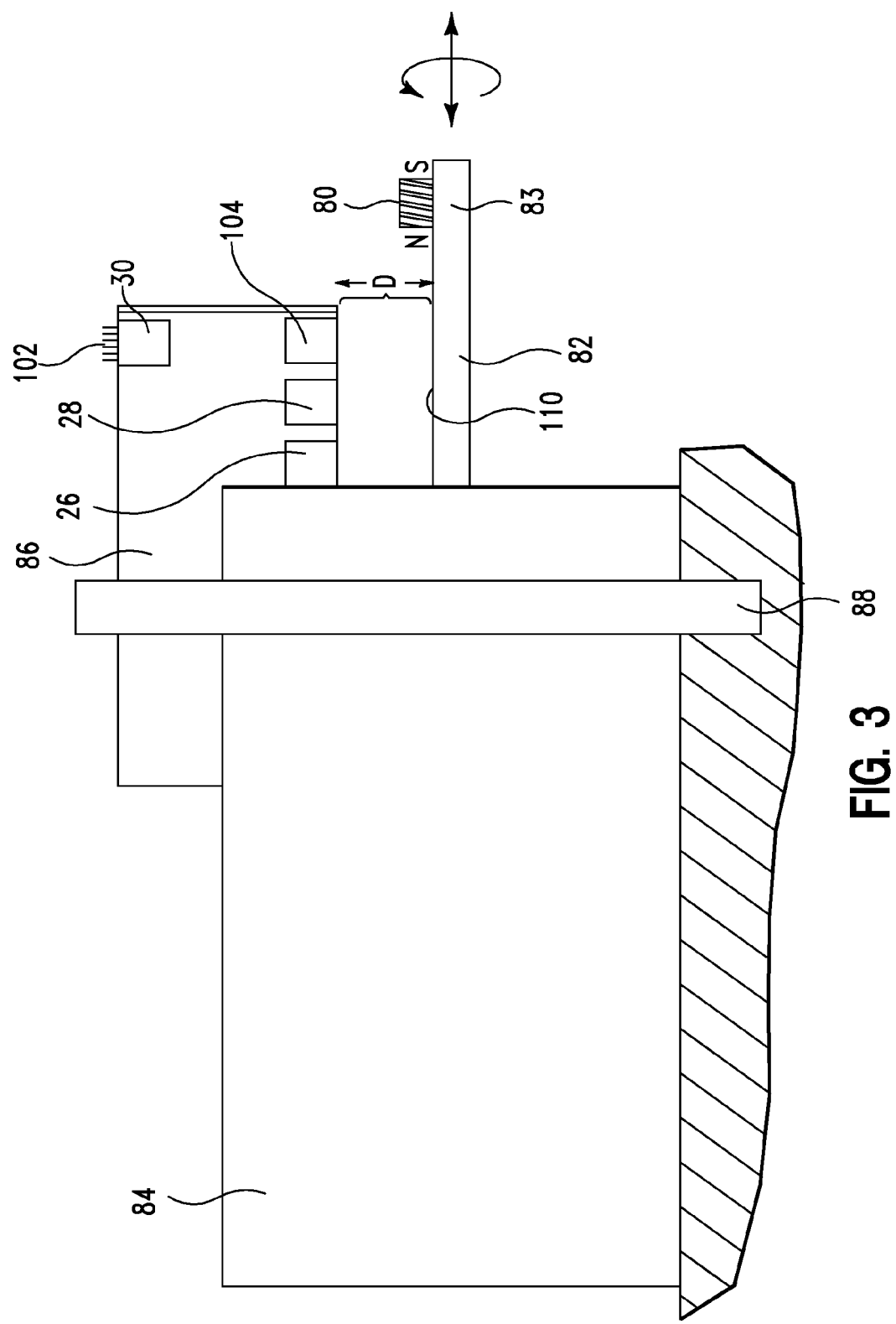
FIG. 3 is a cross sectional view of a measuring tool of the present patent application mounted for measuring linear and/or rotational displacement of a hydraulic actuator rod.

In one embodiment absolute displacement with respect to a fixed location can be obtained by providing permanent magnet 80 on moveable target 82, as shown in FIG. 3. In this embodiment, moveable target 82 can be a portion of actuator rod 83 extending into and out of fixed housing 84. Together, housing 84 and actuator rod 83 form a device, such as a hydraulic cylinder, a pneumatic cylinder, or an electric motor.

In this embodiment, measuring tool 20, connected to fixed housing 84 with clamp 88 includes light source 26, imaging device 28, electronic circuit 30, 6 pin connector 32, and Hall effect sensor 104, which provides initial reference position P with respect to permanent magnet 80. As described herein above with respect to the embodiment of FIG. 1, imaging device 28 provides images of imageable features on moveable target 82 that are analyzed by electronic circuit 30 to determine linear and rotational displacement from initial reference position P.

Movement past magnet 80 causes Hall effect sensor 104 to change its output state. Hall effect sensor 104 is connected to electronic circuit 30 such that the processor (not shown) within circuit 30 uses the signal from Hall effect sensor 104 to establish initial reference position P. Further displacements are measured with respect to initial reference position P. Hall effect sensor 104 can be positioned to provide a reference position for translation or rotation or for both. Thus, the processor takes the relative data from the optical sensors and converts it to absolute location and/or orientation with respect to initial reference position P defined by magnet 80 and Hall effect sensor 104.

Figure 4A:
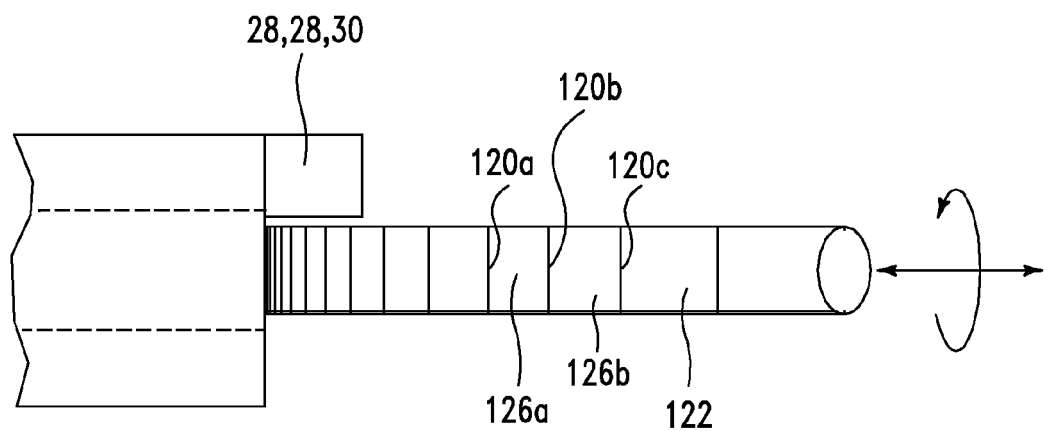
FIG. 4a is a cross sectional view of a measuring tool of the present patent application mounted for measuring linear and/or rotational displacement of a displacement sensor or actuator having etched lines.
Figure 4B:
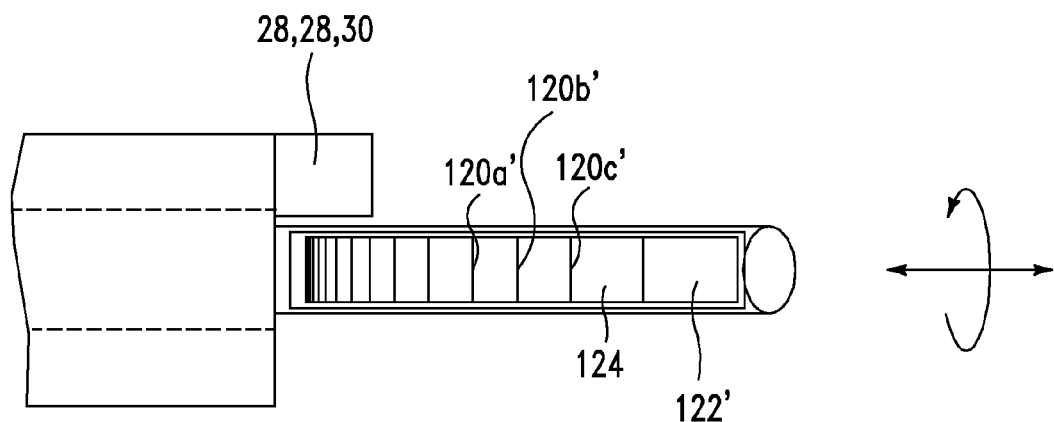
FIG. 4b is a cross sectional view of a measuring tool of the present patent application mounted for measuring linear and/or rotational displacement of a displacement sensor or actuator having a label with printed lines.

Another way that absolute displacement with respect to a fixed location can be obtained is by providing one or more indicator marks 120a, 120b, 120c on moveable target 122 as shown in FIG. 4a. Indicator marks 120a, 120b, 120c have different spacings there between. Thus, the location on moveable target 122 is determined from the spacing between adjacent indicator marks and from the optical measurement of distance from one mark. Indicator marks can extend all the way around moveable target 122 so that they are seen regardless of rotation of moveable target 122. Alternatively, moveable target 122' can include adhesively attached paper label 124, as shown in FIG. 4b, which includes indicator marks 120a', 120b', 120c'. Paper label 124, with indicator marks 120a', 120b', 120c', can extend all the way around moveable target 122. In addition similar reference marks can be provided perpendicular to those shown in FIGS. 4a, 4b for providing a rotational reference.

Electronic circuit 30 can use image data from imaging device 28 to detect presence of indicator marks 120a, 120b, 120c and measure the relative distance between adjacent indicator marks. Using a lookup table with stored spacings, the relative distance between two adjacent indicator marks tells the processor which box 126a, 126b imaging device 28 is looking at. From the direction image data moves in sequential images or from the distance to third line 126c it can tell which direction target 122 is moving. As shown in FIGS. 4a, 4b spacing between adjacent indicator marks 120a, 120b, 120c gets larger in one direction and smaller in the other direction.

Figure 5:
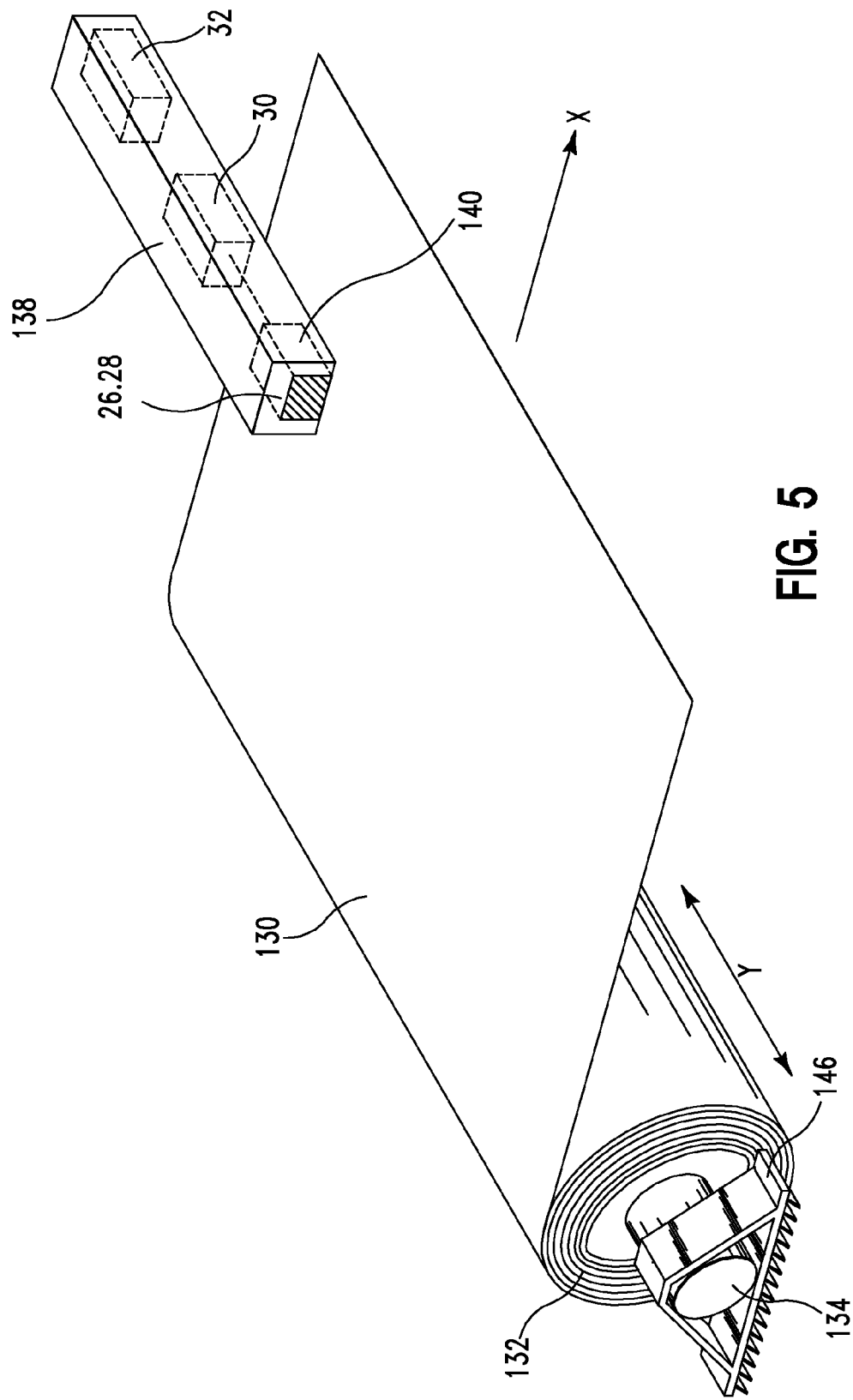
FIG. 5 is a cross sectional view of a measuring tool of the present patent application mounted for measuring linear displacement of a paper extending from a paper roll.

In another embodiment, material 130 is drawn from roll 132 wound around spool 134, as shown in FIG. 5. The direction material 130 moves as it is wound or unwound defines the x axis of this system. Imaging device 28 mounted in fixture 138 takes images of laser light originating from light source 26 and reflected from material 130. Electronic circuit 30 determines length of material drawn from roll 132 based on data provided by imaging device 28. Data from electronic circuit 30 is provided on 6 pin connector 32. Material 130 can be paper, metal, fabric, or any other rolled material. In one embodiment mounting 146 for spool 134 is itself capable of movement along the y axis perpendicular to the x axis causing movement of material 130 in the y direction. Imaging device 28 mounted in fixture 138 can detect and measure this movement as well. Imaging device 28 can also detect and measure a combination of movements in x and y directions simultaneously.

Figure 6:
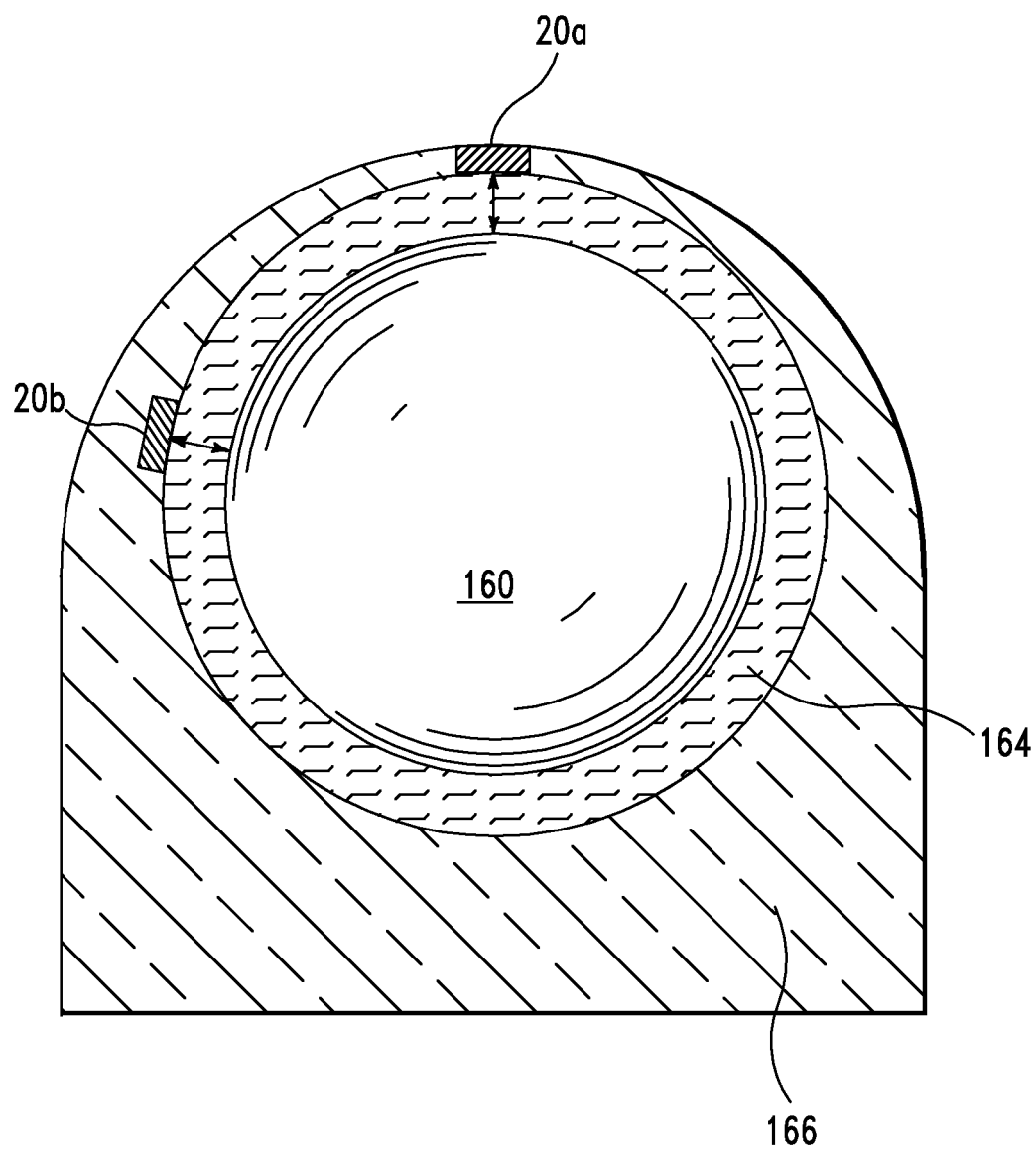
FIG. 6 is a cross sectional view of a measuring tool of the present patent application mounted for measuring rotational displacement of a floating sphere for determining pitch, roll, and compass heading.

In another embodiment two dimensional rotational movements of sphere 160 are measured with measuring tool 20a to give pitch and roll, as shown in FIG. 6. Another measuring tool 20b can also be mounted to measure pitch and compass heading of the sphere, as also shown in FIG. 6. In one embodiment, sphere 160 can be a magnetized ball floating on liquid 164 in housing 166 to provide an optical compass capable of providing all three measurements of orientation. Housing 166 can be connected, for example to a boat.

Figure 7:
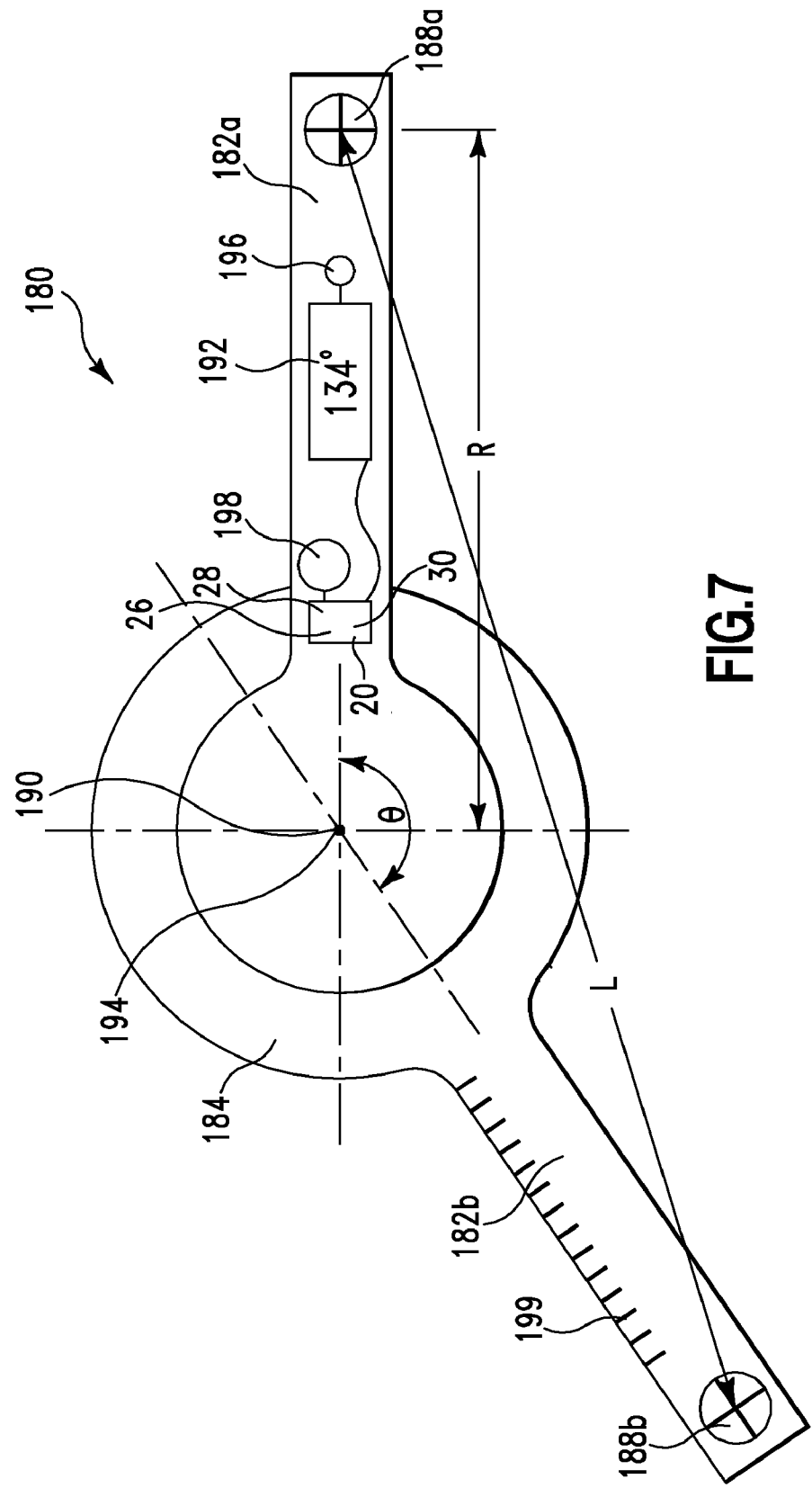
FIG. 7 is a top view of a measuring tool of the present patent application with an optical sensor mounted for measuring an angle between two legs of the tool.

In another embodiment optical measuring stick (goniometer) 180 includes swivelable arm 182a mounted to base 184 that includes base arm 182b, as shown in FIG. 7. Arm 182a and base arm 182b have crossed indicators 188a, 188b that are located a distance R from center point 190 and that can be positioned over any two points that are a distance less than 2R apart. Display 192 connected to measuring tool 20 provides the angle theta between arm 182a and base arm 182b. Measuring tool 20 includes light source 26, imaging device 28, and electronic circuit 30. Light from light source 26 shines on base 184 while imaging device 28 and electronic circuit 30 determine rotation angle of arm 182a with respect to base 184. A reference mark may be provided on base 184 to indicate theta=0 degrees. Electronic circuit 30 can then calculate space L between crossed indicators 188a, 188b from L=2R sin (theta/2). Electronic circuit 30 can be programmed so the user pressing button 196 changes display 192 from showing angle to showing distance. Button 196 can be pressed for an extended period of time to turn on and off power provided by battery 198. The entire tool and display can be programmed to automatically turn off if the system is not used for a programmable time interval to conserve life of battery 198. Arm 182a and base 184, including base arm 182b are transparent and may have marks 199 to provide another ruler.

For biomechanics applications it may be desirable to measure the angular motion of a joint of the body, for example, a finger, wrist, elbow, shoulder, ankle, knee, hip, or spine. In the most comprehensive work, it may be desirable to measure all six degrees of freedom (three translations, three rotations). For many purposes, however, only a subset of the full six degrees-of-freedom are measured, while the others can be ignored or assumed be small, and therefore negligible. For example, a detailed study of motion of a knee or a shoulder may require full six degree-of-freedom measurement of its kinematics. On the other hand, a simple measure of the knee's range-of-motion for the purpose of tracking physical therapy treatments may only require measuring a single degree of freedom, namely flexion/extension angle. The device described herein can be configured to make measurements of the kind needed for each of these applications.

One embodiment of a configuration used to make one or two degree-of-freedom measurements is illustrated in FIG. 8a. Fixed mounting pad 200 is rigidly fixed to flexible wire 202. Second moving mounting pad 204 contains guide hole 206 through which wire 202 can pass with negligible friction. Such a low friction may be achieved with a polished wire moving in a guide hole fabricated of a low friction material, such as teflon. Measuring tool 20 is mounted in moving mounting pad 204 such that surface 210 of wire 202 is located at the optical focal point of its optical elements, light source 26 and imaging device 28. Wire 202 forms the optical target. Measuring tool 20 can measure translation distance and translation direction of wire 202 in either direction along the axis of guide hole 206, as shown by arrow T. Measuring tool 20 can also measure rotation of wire 202 in either direction about the axis of guide hole 206, as shown by arrow R.

Measuring tool 20 can be used to measure a single degree of freedom of a joint, such as the flexion angle of a wrist, as shown in FIG. 9. In one embodiment, fixed mounting pad 200 is strapped to the hand while moving mounting pad 204 is fixed to the forearm. Pads 200, 204 are located such that flexion of the wrist causes wire 202 to slide within guide hole 206 within moving mounting pad 204 as the wrist's flexion angle is changed. This sliding motion can be measured by measuring tool 20 as a displacement. Spring 208 and stop 210 can be provided to facilitate return movement of wire 202.

As moving mounting pad 204 moves with respect to fixed mounting pad 200, wire 202 is forced to bend and to slide within low friction guide hole 206 of moving mount pad 204. The alignment of the longitudinal axis of wire 202 is constrained at the points where it is fixed to fixed mounting pad 200. The tangent of wire 202 is also fixed at the point where it enters guide hole 206 of moving mount pad 204. The shape that is assumed in between mounting pads 200, 204 will be the one in which total strain energy of wire 202 is the lowest. To achieve this lowest energy state, wire 202 can slide and/or rotate within guide hole 206 and take on different radii of curvature in between mounting pads 200, 204.

Given arbitrary positions and orientations of mounting pads 200, 204 there will, in general, be a unique wire configuration in which wire 202 will reach its lowest energy state. In this embodiment no external forces are applied to wire 202 other than those applied by mounting pads 200, 204. For each flexion angle of the wrist, there will be a unique configuration of wire 202 and a corresponding unique measurement of the position and rotation of wire 202 within guide hole 206. With a lookup table or with calibration coefficients, either of which may be obtained empirically from measurements of wire displacement and angle providing that displacement, this measurement of the wire's position within guide hole 206 as provided by measuring tool 20, can be transformed into a measure of the flexion angle of the wrist.

Figure 10A:
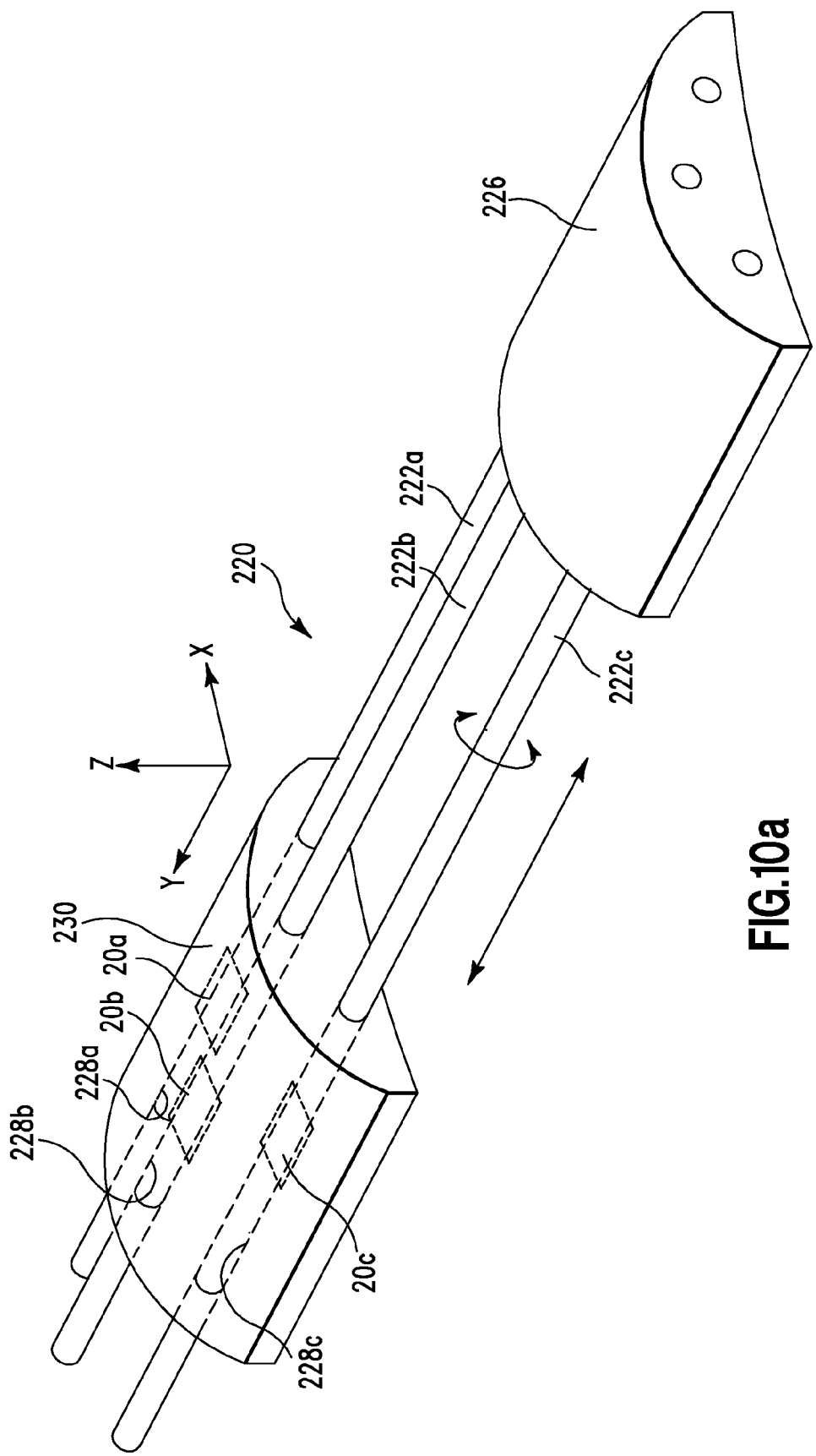
FIGS. 10a and 10b are three dimensional views of measuring tools of the present patent application mounted for measuring linear and/or rotational displacement of one portion of an object with respect to another portion of the object.
Figure 10B:
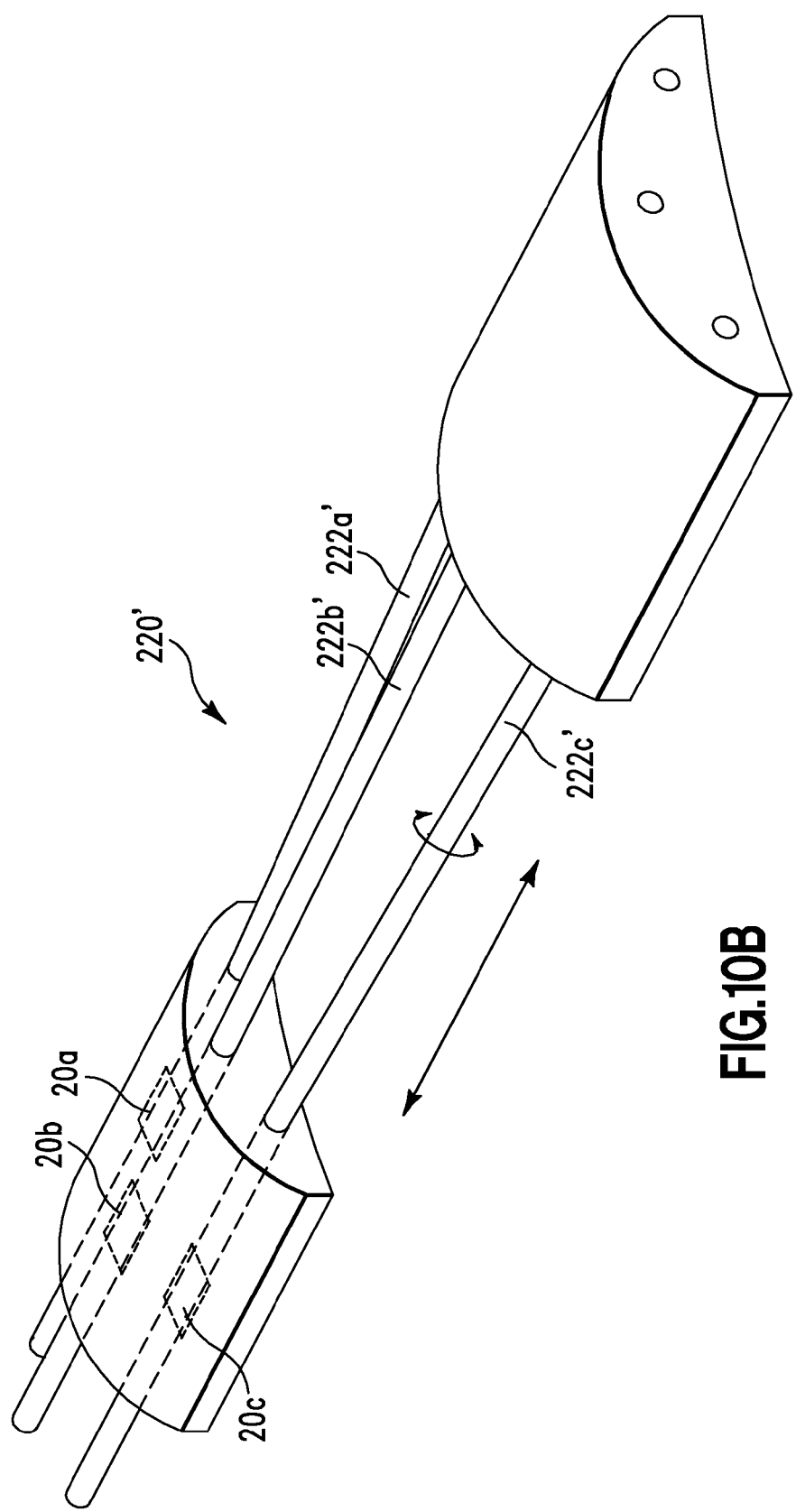

A system consisting of a single wire and a single optical measuring tool can measure two degrees-of-freedom, displacement and rotation of the wire. To adequately measure motions having three or four degrees-of-freedom, multi-wire sensor systems can be used, as shown in FIG. 10a. This embodiment provides system 220 containing three wires 222a, 222b, 222c, each with its own optical sensor, measuring tool 20a, 20b, 20c. In this embodiment wires 222a, 222b, 222c are not all coplanar. Since the three wires are all parallel the system can detect only one degree of translation but it can detect three degrees of rotation. For measuring all six degrees of freedom, wires 222a', 222b', 222c' of system 220' would be positioned at a non-zero angle with respect to each other so they are not parallel, as shown in FIG. 10b. As in the single wire system of FIGS. 8 and 9, each wire 222a-222c is rigidly attached to fixed mounting pad 226, and slides within low friction guide holes 228a, 228b, 228c in moving mounting pad 230. The configuration of each wire 222a-222c after moving mounting pad 230 has moved will be the one in which strain energy of each wire 222a-222c is minimized.

Rotation of moving mounting pad 230 with respect to fixed mounting pad 226 around the x axis shown in FIG. 10a will cause displacement in opposite directions for wires 222b compared to wires 222a and 222c. Rotation of moving mounting pad 230 around the z axis will cause displacement in opposite directions for wires 222a and 222c. Rotation of moving mounting pad 230 around the y axis will cause both displacement and rotation in the same direction for wires 222a, 222b, and 222c. Displacement of moving mounting pad 230 along the y axis will cause displacement in the same direction for wires 222a, 222b, and 222c but no rotation of these wires.

Position and rotation of each wire 222a, 222b, and 222c within its guide hole 228a-228c is determined from the output of corresponding measuring tool 20a-20c. The relative position and orientation of mounting pads 226, 230 is solved for based on calibration coefficients or a lookup table that may be empirically derived from experimental measurements. In another embodiment, numerical techniques can be used to model the apparatus and to determine displacements and rotational angles from measured data.

Figure 8:
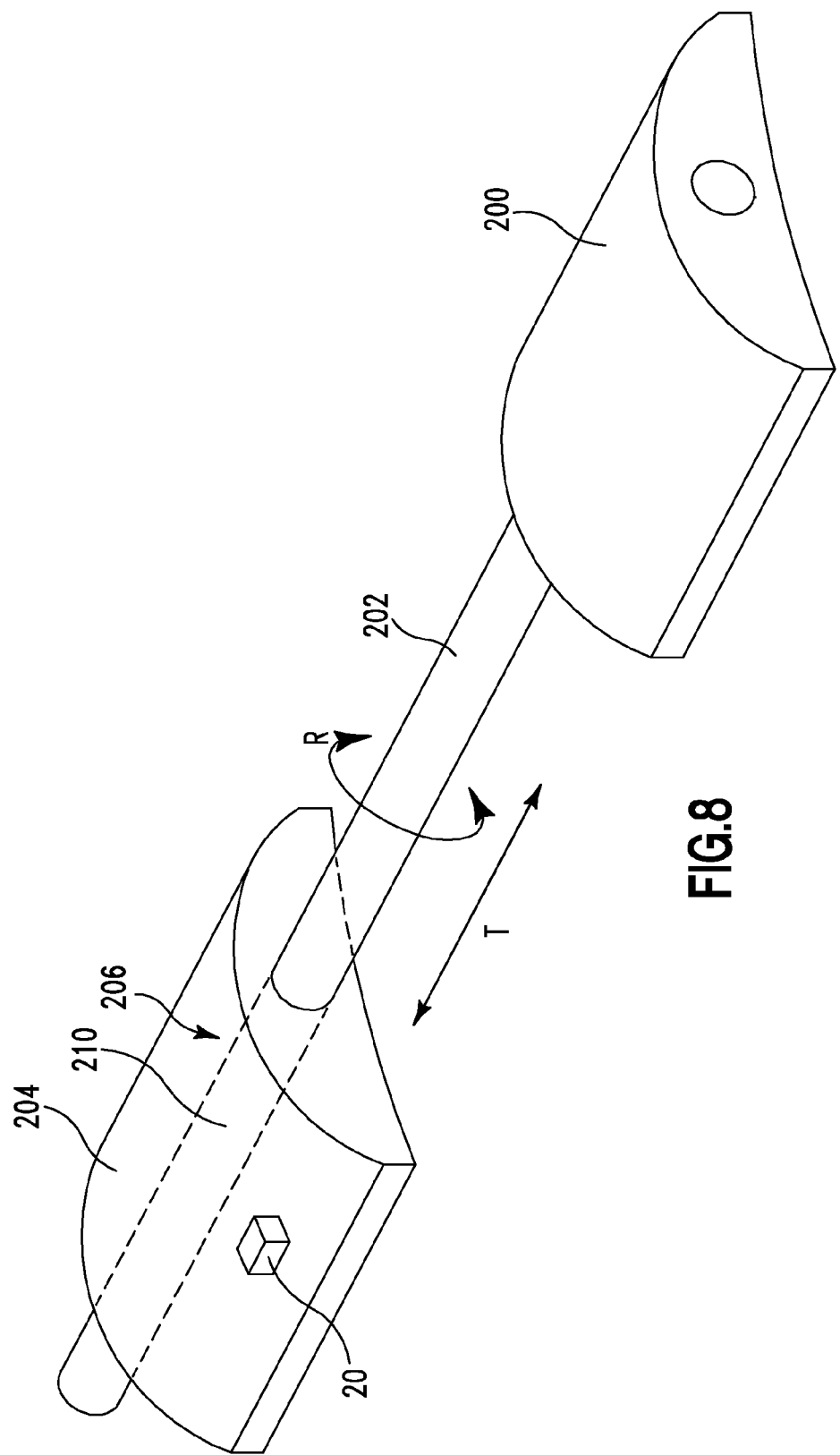
FIG. 8 is a three dimensional view of a measuring tool of the present patent application mounted for measuring linear and/or rotational displacement of one portion of an object with respect to another portion of the object.

In another embodiment the apparatus of FIG. 8, FIG. 10a, or FIG. 10b is mounted in a robotic device that can twist and translate to many known positions of rotation and translation. Translation and rotation data for the wire of FIG. 8 or each of the three wires of FIGS. 10a, 10b as measured by measuring tool 20 and electronic circuit 30 is logged along with the known position and orientation provided by the robotic device to generate a lookup table. Thus, the processor is essentially trained to learn position and orientation from the data measured by measuring tool 20 for the wire or wires. The processor can also interpolate between known positions and orientations to estimate positions and orientations between those measured during the training.

Figure 11:
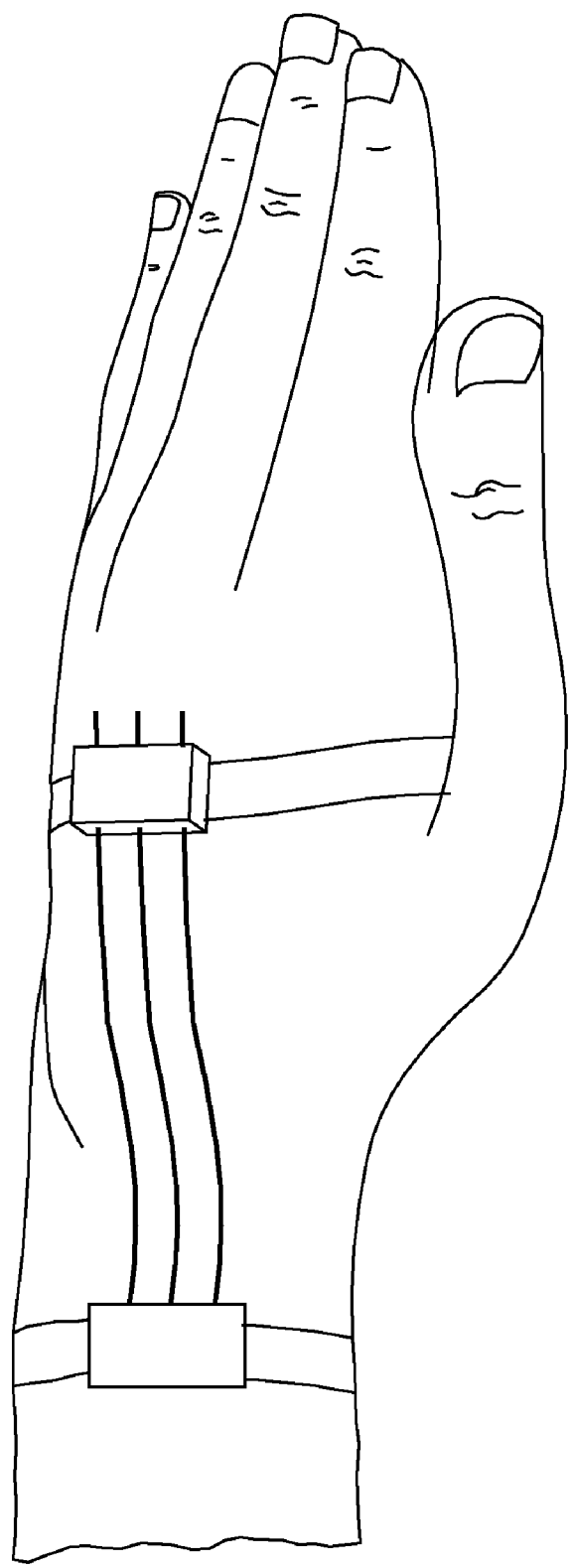
FIG. 11 is a three dimensional view of a hand, wrist, and arm of a person with a measuring tool of the present patent application mounted thereon for measuring rotational displacement of the wrist.
Figure 12B:
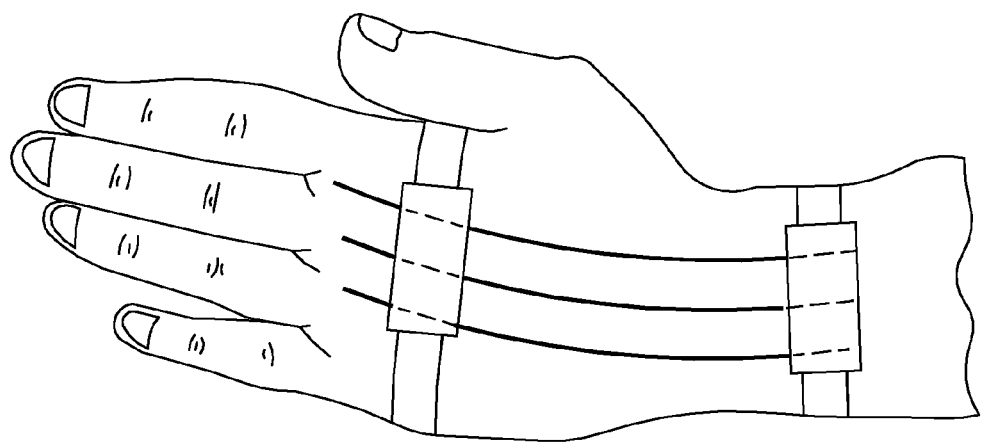
FIGS. 12a and 12b are three dimensional views of a hand, wrist, and arm of a person with a measuring tool of the present patent application mounted thereon for measuring rotational displacement of the wrist.
Figure 12A:
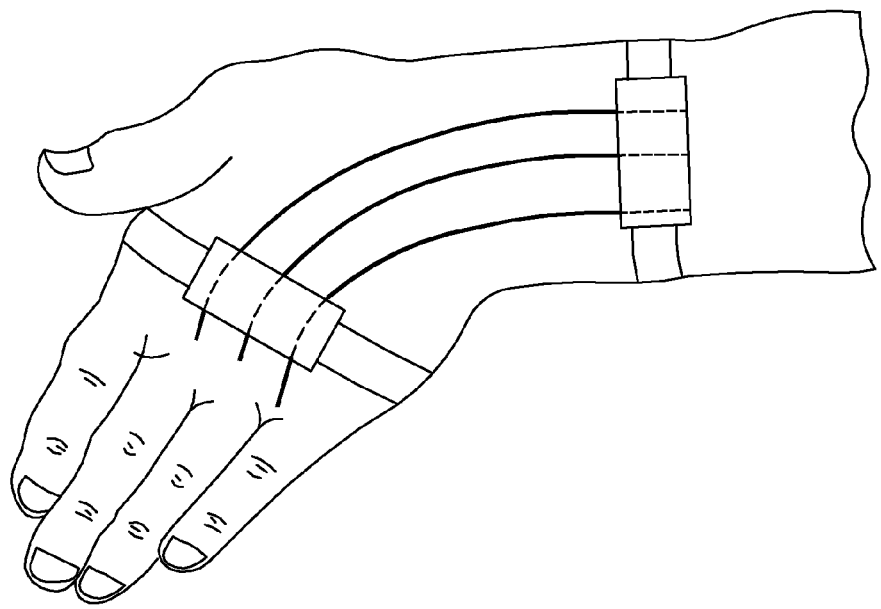
Figure 13:
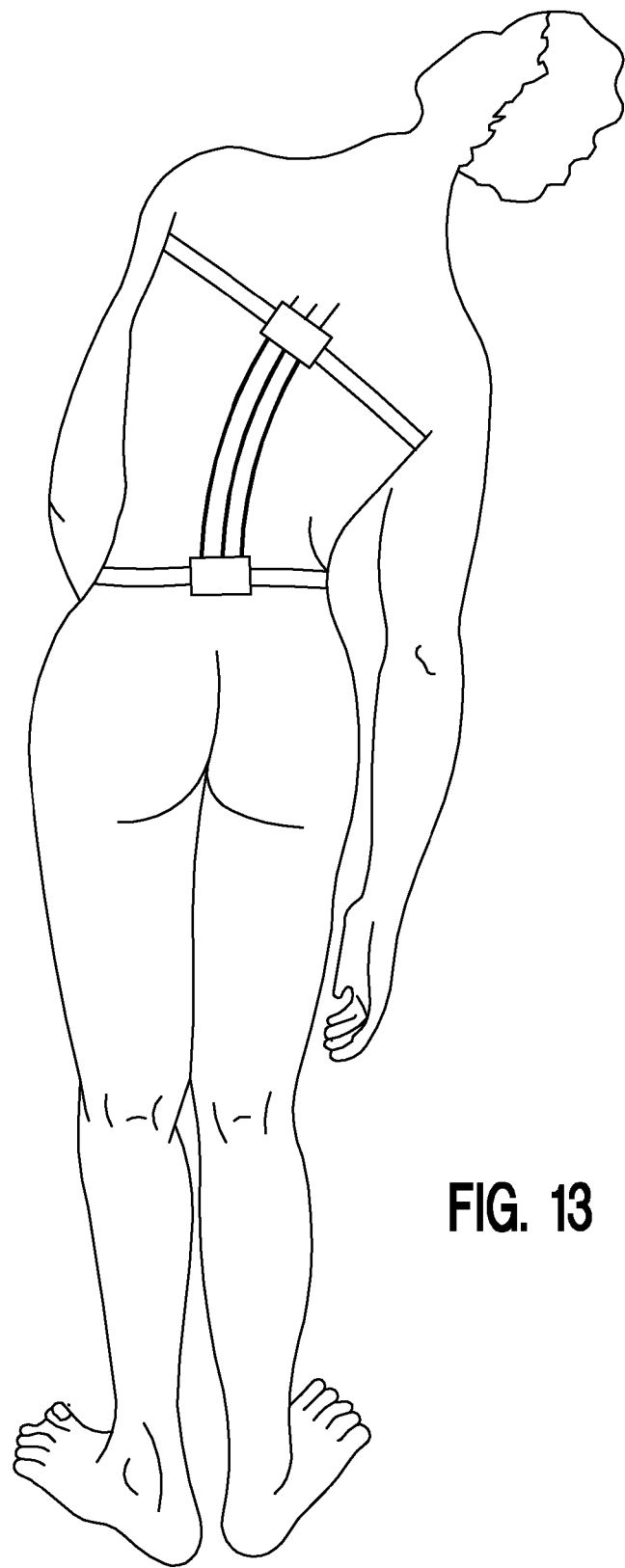
FIG. 13 is a three dimensional view of a person with a measuring tool of the present patent application mounted thereon for measuring lateral bending of the spine.
Figure 14:
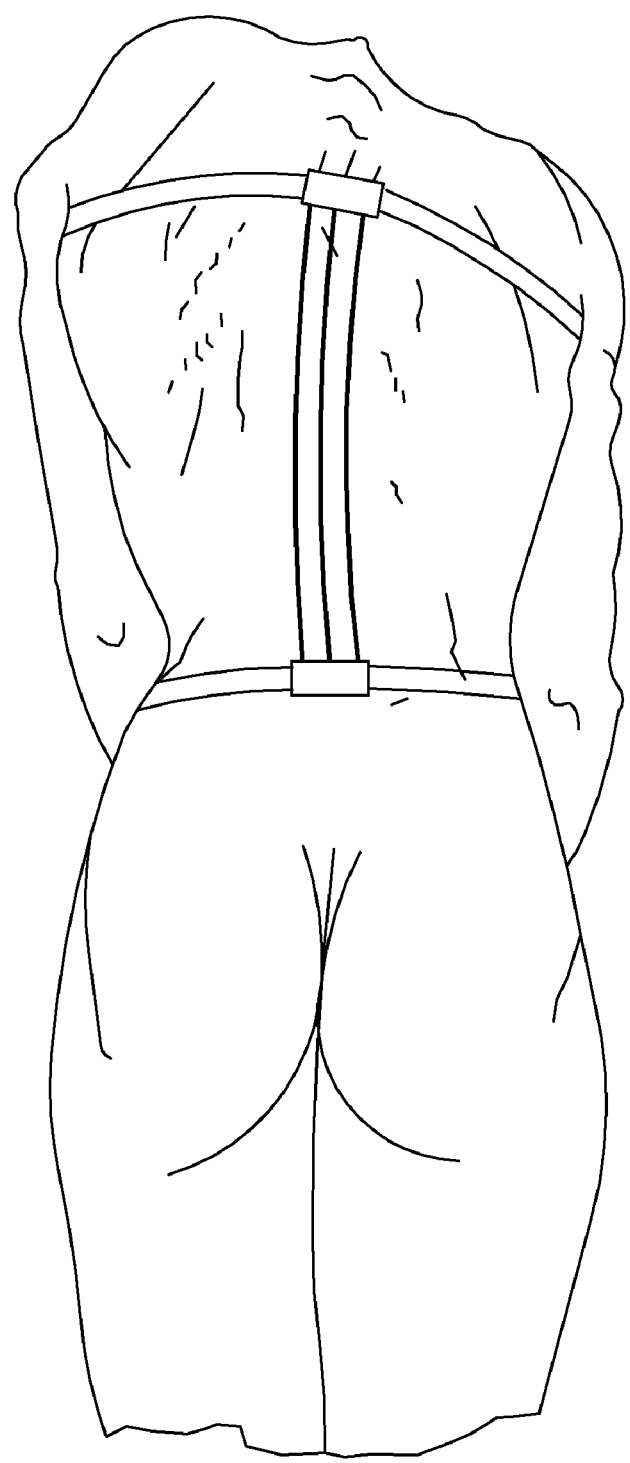
FIG. 14 is a three dimensional view of a person with a measuring tool of the present patent application mounted thereon for measuring lateral bending, forward bending, and/or axial twisting of the spine.
Figure 15:
FIG. 15 is a three dimensional view of a person with a measuring tool of the present patent application mounted thereon for measuring forward bending of the spine.

The use of a three wire system for measuring two rotational degrees-of-freedom motion of the wrist is shown in FIG. 11 and FIGS. 12a, 12b. The use of a similar three wire system for measuring two or three rotational degrees-of-freedom motion of the spine is shown in FIGS. 13-15. The lateral bending of FIG. 13 provides rotation around an axis through the belly button. The forward bending of FIG. 15 provides rotation around an axis extending through the two hips. The axial twisting of FIG. 14 provides rotation around an axis extending along the spine or several axes along the different portions of the spine. The movement shown in FIG. 14 includes a combination of axial twisting, lateral bending, and forward bending.

Figure 16:
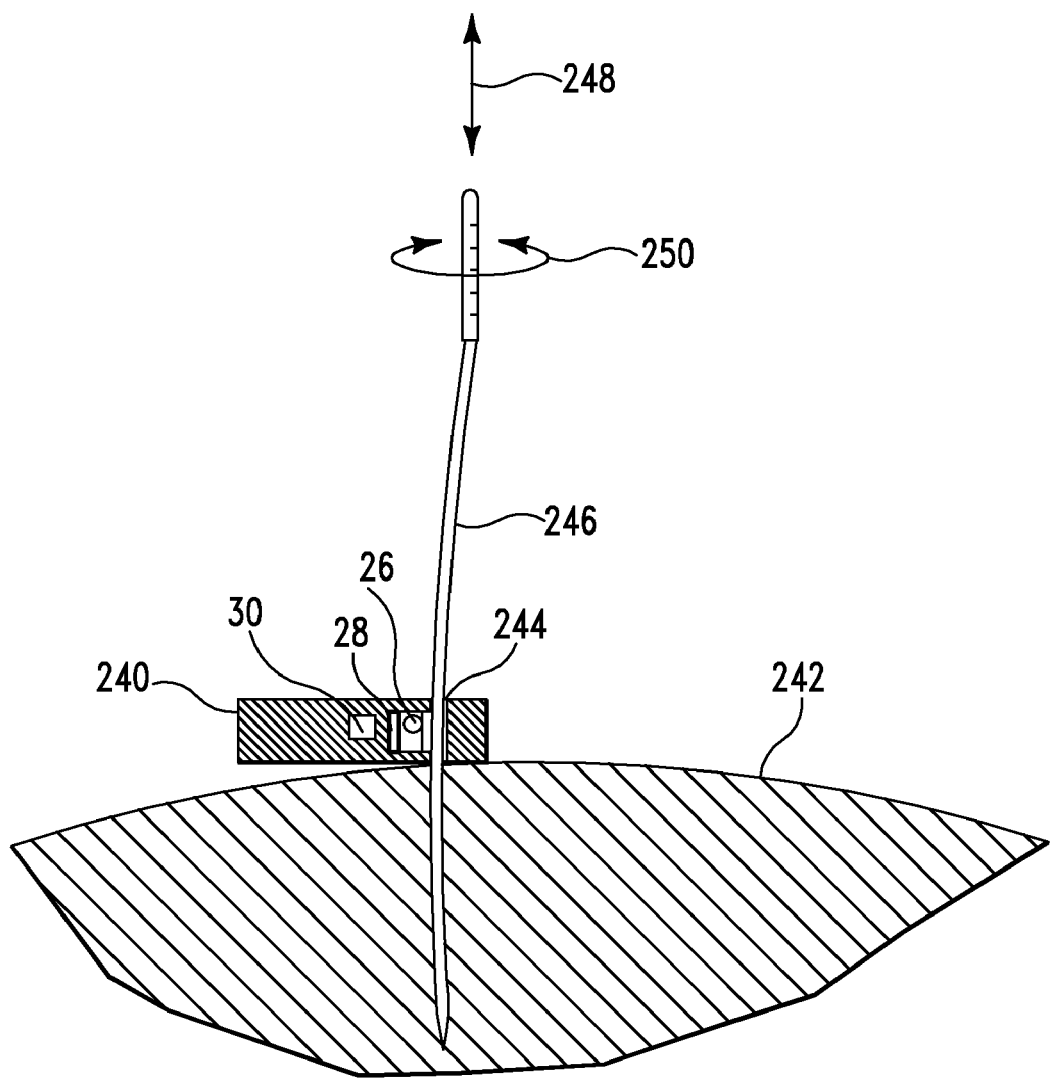
FIG. 16 is a cross sectional view of a measuring tool of the present patent application mounted for measuring linear and/or rotational displacement of an acupuncture needle.

In one embodiment, light source 26, and imaging device 28, are mounted in housing 240 which is held against skin 242 of a human or animal subject, as shown in FIG. 16. Housing 240 includes guide hole 244 through which acupuncture needle 246 is passed. Guide hole 244 is configured such that the surface of acupuncture needle 246 is in the focal plane of imaging device 28. Imaging device 28 can therefore measure the translation 248 and rotation 250 of acupuncture needle 246 as it is inserted into the subject's tissue and rotated.

While the disclosed methods and systems have been shown and described in connection with illustrated embodiments, various changes may be made therein without departing from the spirit and scope of the invention as defined in the appended claims.

What is claimed is:

1. A system, comprising a measuring tool, a fixture, and a rotatable target, wherein said measuring tool includes a light source, an imaging device, and an electronic circuit, wherein said fixture allows said rotatable target to rotate about an axis, wherein said rotatable target includes a surface having microscopic asperities, wherein said imaging device is mounted to provide a sequence of images derived from said microscopic asperities, wherein said electronic circuit is connected to said imaging device for measuring rotation of said rotatable target from said sequence of images.

2. A system as recited in claim 1, wherein said light source is coherent.

3. A system as recited in claim 1, wherein said light source shining on said surface having said microscopic asperities provides a speckle pattern and wherein each image of said sequence of images includes said speckle pattern.

4. A system as recited in claim 1, wherein said electronic circuit includes a processor.

5. A system as recited in claim 1, wherein said electronic circuit includes calibration to convert a signal derived from said sequence of images to an angle.

6. A system as recited in claim 5, further comprising a memory device storing at least one from the group consisting of calibration coefficients and a look-up table, wherein said calibration is provided by said memory device.

7. A system as recited in claim 1, further comprising a reference feature on said target.

8. A system as recited in claim 7, further comprising a magnetic sensor, wherein said reference feature includes a magnet, wherein said magnetic sensor is mounted to determine location of said magnet.

9. A system as recited in claim 8, wherein said magnetic sensor is positioned for allowing determining absolute motion based on said location of said magnet and based on said measured motrotation.

10. A system as recited in claim 9, wherein said magnetic sensor includes a Hall effect sensor.

11. A system as recited in claim 7, wherein said reference feature includes a mark.

12. A system as recited in claim 11, wherein said rotatable target includes an adhesive label, wherein said mark is on said label.

13. A system as recited in claim 11, further comprising a plurality of said marks.

14. A system as recited in claim 13, wherein said plurality of marks have different spacings there between.

15. A system as recited in claim 11, wherein said imaging device detects presence of said mark to correct for accumulated errors in output.

16. A system as recited in claim 1, wherein said rotatable target is constrained to translation along said axis and rotation about said axis.

17. A system as recited in claim 1 further comprising a circuit for determining at least one from the group consisting of angular velocity and angular acceleration of said target.

18. A system as recited in claim 1, wherein said target includes an actuator rod.

19. A system as recited in claim 18, wherein said actuator rod is an actuator rod of at least one from the group consisting of a hydraulic cylinder, a pneumatic cylinder, and a motor.

20. A system as recited in claim 1, wherein said target includes a portion of at least one from the group consisting of a string pot and a tape measure.

21. A system as recited in claim 1, wherein said target includes a portion of an acupuncture needle.

22. A system as recited in claim 1, wherein said target includes a portion of at least one from the group consisting of a wire, a chord, an optical cable, a string, a needle, and a pipe.

23. A system as recited in claim 1, further comprising a controller for controlling movement of said target, wherein data derived from said measuring tool is provided as feedback to said controller.

24. A system as recited in claim 1, further comprising a connector.

25. A system as recited in claim 24, wherein said connector includes pins for power, ground and digital data out.

26. A system as recited in claim 1, wherein said measuring tool is connected to said fixture.

27. A system as recited in claim 26, wherein said fixture includes an opening for light from said light source to travel from said light source to said surface and for reflected light to enter said imaging device.

28. A system as recited in claim 1, wherein said imaging device is located a fixed distance from said moveable target.

29. A system as recited in claim 1, wherein said fixture allows said rotatable target to rotate about a first axis and to rotate about a second axis perpendicular to said first axis.

30. A system as recited in claim 1, wherein said fixture allows said rotatable target to translate along said axis.

31. A system as recited in claim 1, wherein said electronic circuit is programmed to use said rotation measurement to calculate another parameter.

32. A system as recited in claim 31, wherein said other parameter includes separation distance.

33. A system, comprising a measuring tool, a first fixture, a moveable target, and a first axis, wherein said measuring tool includes a light source, an imaging device, and an electronic circuit, wherein said first fixture constrains said moveable target to at least one from the group consisting of translation along said first axis and rotation about said first axis, wherein said moveable target includes a surface having microscopic asperities, wherein said imaging device is mounted to provide a sequence of images derived from said microscopic asperities, wherein said electronic circuit is connected to said imaging device for measuring movement of said moveable target from said sequence of images.

34. A system as recited in claim 33, wherein said first fixture constrains said moveable target to translation along said first axis.

35. A system as recited in claim 33, wherein said first fixture constrains said moveable target to rotation about said first axis.

36. A system as recited in claim 33, wherein said first fixture constrains said moveable target to translation along said first axis and rotation about said first axis.

37. A system as recited in claim 33, further comprising a second fixture, wherein said first fixture is mounted on said second fixture, wherein said second fixture constrains said moveable target to translation along a second axis perpendicular to said first axis.

38. A system as recited in claim 33, wherein said target includes a portion of a roll of a material.

39. A system as recited in claim 38, wherein said material includes at least one from the group consisting of paper, metal, and plastic.

40. A system as recited in claim 33, wherein said target includes an actuator rod.

41. A system as recited in claim 40, wherein said actuator rod is an actuator rod of at least one from the group consisting of a hydraulic cylinder, a pneumatic cylinder, and a motor.

42. A system as recited in claim 33, wherein said target includes a portion of at least one from the group consisting of a string pot and a tape measure.

43. A system as recited in claim 33, wherein said target includes a portion of an acupuncture needle.

44. A system as recited in claim 33, wherein said target includes a portion of at least one from the group consisting of a wire, a chord, an optical cable, a string, a needle, and a pipe.

45. A system as recited in claim 33, wherein said measuring tool provides measurement of more than two degrees of freedom.

46. A system, comprising an elongate member and a measuring tool, wherein said measuring tool includes a light source, an imaging device, and an electronic circuit, wherein said elongate member has a surface, wherein said imaging device is mounted to image said surface, wherein said measuring tool measures at least one from the group consisting of translation and rotation of said elongate member from said images of said surface.

47. A system as recited in claim 45, wherein said elongate member includes one from the group consisting of a wire, a thread, a filament, a needle, a catheter, a tube, a pipe, a rod, and a tape.

48. A system as recited in claim 45, wherein said needle is an acupuncture needle.

49. A system as recited in claim 45, wherein said elongate member includes wire, further comprising a plurality of said wires, wherein said measuring tool measures at least one from the group consisting of translation along more than one axis and rotation around more than one axis.

50. A system as recited in claim 48, wherein said plurality of wires are non-parallel with respect to each other.

51. A system as recited in claim 45, wherein said surface has microscopic asperities, wherein said imaging device is mounted to provide a sequence of images derived from said microscopic asperities.

52. A system as recited in claim 45, wherein said elongate member has a length to width ratio of more than ten to one.

53. A system as recited in claim 45, wherein said elongate member has a length to width ratio of more than one hundred to one.

54. A system, comprising at least one fixture, a plurality of measuring tools and a plurality of moveable targets, wherein each said measuring tool includes a light source and an imaging device, wherein each said moveable target includes a surface having microscopic asperities, wherein each said imaging device is mounted to provide a sequence of images derived from said microscopic asperities, wherein said at least one fixture constrains movement of said moveable targets relative to said imaging devices for measuring movements of said moveable targets from said sequences of images.

* * * * *